United States Patent [19]

Takada et al.

[11] Patent Number: 5,976,597
[45] Date of Patent: *Nov. 2, 1999

[54] BASIC PROTEIN COMPOSITION, BASIC PEPTIDE COMPOSITION AND APPLICATION THEREOF

[75] Inventors: Yukihiro Takada, Kawagoe; Seiichiro Aoe, Sayama; Hiroaki Matsuyama, Kawagoe; Ken Kato, Ohmiya; Junichi Yamamura, Kawagoe, all of Japan

[73] Assignee: Fujino Patent Attorney, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/785,326

[22] Filed: Jan. 21, 1997

[30] Foreign Application Priority Data

Jan. 23, 1996 [JP] Japan .................................. 8-028459

[51] Int. Cl.$^6$ .............................. A23C 1/00; A23C 7/04; A23C 9/146; A23C 9/14
[52] U.S. Cl. .......................... 426/491; 426/271; 426/580; 426/587; 426/588; 426/590; 514/773; 514/775
[58] Field of Search .................................... 426/590, 271, 426/491, 580, 587, 588; 514/773, 775

[56] References Cited

U.S. PATENT DOCUMENTS

| | | | |
|---|---|---|---|
| 3,970,520 | 7/1976 | Feldman et al. | 195/29 |
| 4,107,334 | 8/1978 | Jolly | 426/7 |
| 5,149,647 | 9/1992 | Burling | 435/192 |
| 5,405,756 | 4/1995 | Naito et al. | 435/68.1 |
| 5,516,675 | 5/1996 | Uchida et al. | 435/192 |

FOREIGN PATENT DOCUMENTS

| | | | |
|---|---|---|---|
| 0 556 083 A1 | 8/1993 | European Pat. Off. | C07K 3/22 |
| 0 573 668 A1 | 12/1993 | European Pat. Off. | A61K 37/02 |
| 0 704 218 A2 | 4/1996 | European Pat. Off. | A61K 38/01 |
| 2303457 | 12/1990 | Japan . | |
| 04183371 | 6/1992 | Japan . | |
| 07033668 | 2/1995 | Japan . | |
| 08165249 | 6/1996 | Japan . | |
| WO93/13676 | 7/1993 | WIPO | A23J 1/20 |

OTHER PUBLICATIONS

K. Kussendrager, "Lactoferrin and Lactoperoxydase, Bioactive Milk Proteins" *IFI NR.6*, pp. 17–21 (1993).

S. Rudloff et al., "Calcium Retention from Milk–Based Infant Formulas, Whey–Hydrolysate Formula, and Human Milk in Weanling Rhesus Monkeys" *AJDC* 144:360–363 (1990).

Francis et al. 1995 J Dairy Sci 78 pages 1209–1218, May 1995.

European Patent Office Search Report, App. No. EP 97 10 0945, Aug. 20, 1998, 3 pgs.

(List continued on next page.)

*Primary Examiner*—Frank C. Eisenschenk
*Assistant Examiner*—Mary K Zeman
*Attorney, Agent, or Firm*—Testa, Hurwitz & Thibeault, LLP

[57] ABSTRACT

The present invention provides a basic protein and a basic peptide composition which can be administered orally and has the ability to stimulate osteoblast proliferation, strengthen bone and inhibit bone resorption. Said basic protein has the following properties: (1) a molecular weight distribution of is 2,000–24,000; (2) an isoelectric point distribution of is 7.5–11; and (3) it is comprised of more than 10% of basic amino acids. Said composition can be obtained by the following steps: After milk, or raw material derived from milk, is loaded onto a cation exchange resin column, a fraction is obtained by eluting with an eluent of 0.1–1.0M salt concentration, precipitate removed by (i) heating to over 75° C., (ii) by adding alcohol so that the final concentration thereof is 10–50% or (iii) by adding salts so that the final concentration thereof will be more than 0.2M; and the supernatant thereof containing the basic protein fraction recovered.

9 Claims, 4 Drawing Sheets

(MEAN ±SD)

OTHER PUBLICATIONS

Yukihiro Takada et al., "Whey Protein Stimulates the Proliferation and Differentiation of Osteoblastic MC3T3–E1 Cells," Biomedical and Biophysical Research Communications, 223, pp. 445–449 (1996).

Database WPI, Section Ch, Week 9635, "Bone Strengthing Composition for Increasing Calcium Absorption, Osteoporosis—Contains Basic Protein Fraction and Calcium Derived from Milk, Especially Useful for Children," Derwent Publications Ltd., London, GB, Class B04, AN 96–350156, XP–002073914.

BASIC PROTEIN COMPOSITION, BASIC PEPTIDE COMPOSITION AND APPLICATION THEREOF

FIELD OF THE INVENTION

The present invention relates to a milk-derived basic protein composition having the activity of stimulating osteoblastic proliferation, strengthening bone and inhibiting bone resorption. In addition, the present invention relates to a milk-derived basic peptide composition which is obtained from the milk-derived protein composition by protease degradation and which has the activity described above. Further, the present invention also relates to foods, drinks, medicines and feeds which comprise the milk-derived basic protein composition and/or the basic peptide composition.

BACKGROUND OF THE INVENTION

Coincident with an increase in human life-span is the recent increase in the incidence of metabolic bone diseases, such as osteoporosis, bone fracture, and bone pain etc. In bone tissue, bone formation and bone resorption are always taking place. While the balance of bone formation and bone resorption takes place in one's youth, bone resorption exceeds bone formation due to various causes as one ages, ("uncoupling"). Prolonged bone resorption causes bone tissue to become fragile, resulting in metabolic bone diseases, such as osteoporosis, bone fracture, bone pain, etc. Accordingly, if uncoupling could be inhibited, metabolic bone diseases such as osteoporosis, bone fracture, bone pain, etc. may be prevented.

Conventional methods of preventing or treating metabolic bone diseases by inhibiting uncoupling include, but are not limited to, (1) dietary calcium supplementation, (2) light exercise, (3) sunbathing and (4) medicinal therapy, etc. are exemplified. Calcium supplements include calcium salts, such as calcium carbonate, calcium phosphate, etc., and naturally occurring calcium-containing preparations, such as bovine bone powder, egg shell, fish bone powder, etc. They are, however, not necessarily suitable for oral administration. Light exercise, jogging or walking are also recommended. However, these activities are troublesome to a person who has become weak or is an immobilized elderly person. Sunbathing is believed to be beneficial for supplementing the active form of vitamin $D_3$ but is not sufficient as therapy. A medicinal therapy, such as 1α-hydroxyvitamin $D_3$ and/or calcitonin, may be used as an effective treatment for osteoporosis. However, these compounds are medicines and can not be used as food supplements.

The present inventors have discovered that a fraction obtained from whey protein was effective for strengthening bone (Japanese published unexamined patent application No. 183371 (1992)). Further, the present inventors found that a subfraction obtained from the above bone strengthening fraction by treating with ethanol, heating, treating with salts or treating with ultrafiltration membrane was effective for stimulating proliferation of osteoblasts and for strengthening bone (Japanese published unexamined patent application No. 176715 (1993), Japanese published unexamined patent application No. 320066 (1993)). In addition, the present inventors found that the basic protein fraction present at very low levels in milk was able to stimulate proliferation of osteoblasts, strengthen bone and prohibit bone resorption (Japanese patent application No. 207509 (1995)).

The present inventors found that a basic protein composition obtained from milk-derived basic protein fractions by various kinds of treatment thereof had the activity of stimulating osteoblast proliferation, strengthening bone and inhibiting bone resorption. Further, the inventors found that a basic peptide composition obtained from the above basic protein composition by protease degradation also had the activity of stimulating osteoblast proliferation, strengthening bone and inhibiting bone resorption.

SUMMARY OF THE INVENTION

An object of the present invention is to provide a basic protein composition, obtained from treating milk-derived basic protein fractions in various ways, which has the activity of stimulating osteoblastic proliferation, strengthening bone and inhibiting bone resorption. The milk-derived basic protein composition of the present invention has the following properties:

(1) the molecular weight distribution thereof determined by SDS-polyacrylamide electrophoresis is 2,000–24,000 daltons;
(2) the isoelectric point distribution thereof is 7.5–11;
(3) the amino acid composition thereof comprises 10% basic amino acids; and
(4) the activity of stimulating osteoblast proliferation, strengthening bone and inhibiting bone resorption.

Another object of the present invention is to provide a milk-derived basic peptide composition obtained by protease digestion of the basic protein composition, having the activity of stimulating osteoblast proliferation, strengthening bone and inhibiting bone resorption.

DETAILED DESCRIPTION OF THE INVENTION

The basic protein composition of the present invention is obtained from basic protein fractions, which are present only in a very small amount in milk, and has the activities of stimulating osteoblast proliferation, strengthening bone and inhibiting bone resorption. The milk-derived basic protein composition has a molecular weight distribution determined by SDS-polyacrylamide gel electrophoresis of 2,000–24,000 and an isoelectric point distribution of 7.5–11. This basic protein is comprised of more than 10% basic amino acids.

This basic protein composition can be obtained by the following steps:

After milk or raw material derived from milk is loaded onto a cation exchange resin column, a fraction is obtained by eluting the column with an eluent with a 0.1–1.0M salt concentration and is precipitated (i) by heating over 75° C., (ii) by adding alcohol so that the final concentration thereof is 10–50% or (iii) by adding salts so that the final concentration thereof will be more than 0.2M; and the supernatant thereof can be recovered.

Alternatively, the basic protein composition can also be obtained by ultrafiltration of a fraction eluted with an eluent with a 0.1–1.0M salt concentration using an ultrafiltration membrane with a molecular weight cut off of greater than 30,000 and by recovering the filtrate.

Milk or milk-derived raw materials useful for obtaining the basic protein composition of the present invention may include whole cow milk, breast milk, goat milk, and sheep milk, or reduced and skim forms or whey thereof.

Most of the basic protein composition present in milk comprises lactoferrin and lactoperoxidase, which can be obtained from milk by loading the composition onto a cation exchange resin followed by elution with an eluent of 0.1–1.0M salt concentration. The present inventors found that the lactoferrin or lactoperoxidase did not have the activities of stimulating osteoblastic proliferation, strengthening bone or inhibiting bone resorption.

The inventors then tried to isolate a fraction which had stronger activity for stimulating osteoblast proliferation, strengthening bone and inhibiting bone resorption than those of the milk-derived basic protein by treating the milk-derived basic protein in the following ways:

(1) the eluate of the adsorbed fraction on the above cation exchange resin is heated to over 75° C., the precipitate is removed and the supernatant can be recovered. The eluate is preferably treated by heating at pH6.5–80.

(2) alcohol is added to the above eluate so that the final concentration thereof is 10–50%, the precipitate is removed and the supernatant is recovered. Cooled ethanol is preferably used and treatment at pH6.5–9 is also preferable.

(3) salt is added to the above eluate to bring the final concentration thereof to 0.2M, the precipitate is removed and the supernatant is recovered. After the addition of the salt, the pH of the eluate is preferably adjusted to pH6.5–8.0. Sodium salts such as sodium chloride, potassium salt, ammonium salt, phosphate, bivalent metal salt are preferred.

(4) the above eluent is filtered using an ultrafiltration membrane, which filters out proteins having a molecular weight greater than 30,000 and recovering the filtrate.

The basic protein composition having the aforementioned activities can be efficiently fractionated by the above treatments (1)–(4). The basic protein composition recovered using the above methods has activities of stimulating osteoblastic proliferation, strengthening bone and inhibiting bone resorption and is usually used as powder obtained by lyophilization and can be administered orally.

Alternatively, the basic protein composition of the present invention can be obtained by an appropriate combination of the above (1)–(4) treatments, that is, heating treatment, alcohol treatment, salt treatment and ultrafiltration treatment. The basic protein composition has a molecular weight of 2,000–24,000 dalton as determined by SDS-polyacrylamide gel electrophoresis and an isoelectric point distribution of 7.5–11. Further, the basic protein composition comprises more than 10% basic amino acids.

Further, by treating this basic protein composition with a protease such as pepsin, trypsin, chymotrypsin, or pancreatin, for example, the basic peptide composition can be obtained. The basic peptide composition preferably comprises a basic peptide with a molecular weight less than 10,000 dalton, as determined by SDS-polyacrylamide gel electrophoresis.

The basic protein composition or the basic peptide composition of the present invention, which have the actions of stimulating osteoblast proliferation, strengthening bone and inhibiting bone resorption, can be combined with a food, drink, medicine or feed, which can be taken orally to provide osteoblast proliferation, bone strengthening and bone resorption inhibiting activities The basic protein composition or the basic peptide composition of the present invention can be taken orally in tablet form or in a combined form with milk, juice, yogurt, jelly, bread, ice cream, noodles, sausage etc. For prevention or improvement of osteoporosis or various kinds of metabolic bone diseases, 10–500 mg of the composition can preferably be taken daily. Acute toxicity of the basic protein composition or the basic peptide composition of the present invention was not demonstrated in rats.

Alternatively, the basic protein composition or the basic peptide composition of the present invention can be more preferably taken orally with absorptive calcium salts, such as, for example, calcium chloride, calcium carbonate, calcium lactate, egg shell, and a milk-derived calcium containing composition.

Since the basic protein composition and the basic peptide composition of the present invention can be taken orally and have the activities of stimulating osteoblast proliferation, strengthening bone and inhibiting bone resorption, they are useful as a supplement to food, drink, medicine and feed to prevent or treat various kinds of metabolic bone diseases, such as bone fracture, rheumatism and arthritis, and osteoporosis.

The present invention will be described in more detail infra in reference example 1, examples 1–12 and the test samples which do not limit the scope of the present invention.

Reference Example 1

A column packed with 3,000 g of cation exchange resin, sulfonated chitopearl (Fuji-bouseki), was washed with deionized water. After loading 300 liter of non-sterilized skim milk onto the column at a flow rate of 25 ml/min., the column was washed with deionized water and 21 of 0.05M phosphate buffer (pH 7.0) containing 0.1M sodium chloride to remove unadsorbed protein. The basic protein adsorbed onto the resin was eluted with a 0.1–1.0M sodium chloride gradient using 0.05M phosphate buffer containing 0.1M sodium chloride (pH 7.0) and 0.05M phosphate buffer containing 1.0M sodium chloride (pH 7.0). A reverse osmotic membrane was used to desalt and concentrate the eluted solution, followed by lyophilization, to obtain a powdery basic protein fraction. By repeating this operation 8 times, 2.83 kg of basic protein fraction was obtained. The molecular weight of this main basic protein fraction was 75,000–85,000 dalton, with an isoelectric point distribution of 7.0–8.5. The content of basic amino acids in this basic protein fraction was 17.8%.

EXAMPLE 1

A column packed with 3,000 g of cation exchange resin, sulfonated chitopearl (Fuji-bouseki), was washed with deionized water. After loading 300 l of nonsterilized skim milk onto the column at a flow rate of 100 ml/min., the column was washed with deionized water. The basic protein adsorbed onto the resin was eluted with 0.02M carbonate buffer solution containing 0.87M sodium chloride (pH 6.7). A reverse osmotic membrane was used to desalt and concentrate the eluted solution, followed by lyophilization, to obtain a powdery basic protein fraction. By repeating this operation 8 times, 2.59 kg of basic protein fraction was obtained. The 2.59 kg of the basic protein fraction was dissolved in 50 l of deionized water, the pH adjusted to 7.5 and 45 l of the solution was heated at 80° C. for 10 min. The solution was centrifuged at 5,000×g for 10 min. to remove a precipitate, desalted using a reverse osmotic membrane concentrated and lyophilized to give 530 g of the basic protein composition. The content of basic amino acids in this basic protein composition was 14.2%. Further, the molecular weight of this basic protein was 2,000–23,000 daltons, with an isoelectric point distribution of 8.0–10.5. Each liter of the solution was heated at 75° C., 90° C. or 95° C. for 10 min., followed by centrifugation, treatment with a reverse osmotic membrane and lyophilization to give 34.2 g, 8.3 g and 6.5 g of basic protein compositions respectively whose content of basic amino acids was 16.5%, 14.0% and 14.0% respectively.

EXAMPLE 2

A column packed with 3,000 g of cation exchange resin, sulfonated chitopearl (Fuji-bouseki), was washed with deionized water. After loading 300 l of non-sterilized skim milk onto the column at a flow rate of 100 ml/min., the column was washed with deionized water. The basic protein adsorbed onto the resin was eluted with 0.02M carbonate buffer solution containing 0.87M sodium chloride (pH 6.7). A reverse osmotic membrane was used to desalt and concentrate the eluted solution, followed by lyophilization, to obtain a powdery basic protein fraction. By repeating this operation 8 times, 2.61 kg of basic protein fraction was obtained. The 2.61 kg of the basic protein fraction was dissolved in 50 l of deionized water. To 45 l of the solution, 95% ethanol precooled at −20° C. was added (for a final ethanol concentration) of 30%, followed by centrifugation at 5,000×g for 10 min. to remove a precipitate. The solution was lyophilized to give 453 g of the basic protein composition. The content of basic amino acids in this basic protein composition was 13.6%. Further, the molecular weight of this basic protein composition was 3,000–24,000 dalton, with an isoelectric point distribution of 8.0–11.0. To each one liter of the residual solution, ethanol was added to a final concentration of 10% or 50%, followed by centrifugation and lyophilization to give 39 g and 12 g of basic protein composition respectively, whose content of basic amino acids was 14.6% and 13.6%, respectively.

EXAMPLE 3

A column packed with 3,000 g of cation exchange resin, sulfonated chitopearl (Fuji-bouseki), was washed with deionized water. After loading 300 l of non-sterilized skim milk onto the column at a flow rate of 100 ml/min., the column was sufficiently washed with deionized water. The basic protein adsorbed onto the resin was eluted with 0.02M carbonate buffer solution containing 0.87M sodium chloride (pH 6.7). A reverse osmotic membrane was used to desalt and concentrate the eluted solution, followed by lyophilization, to obtain a powdery basic protein fraction. By repeating this operation 8 times, 2.35 kg of basic protein fraction was obtained. The 2.35 kg of the basic protein fraction was dissolved in 50 l of deionized water, the pH adjusted to 7.5 and 45 l of the solution was treated with sodium chloride for a final sodium chloride concentration of 1.0M. The solution was centrifuged at 5,000×g for 10 min. to remove a precipitate, and the fraction resuspended in 20 l of distilled water. A reverse osmotic membrane was used to desalt and concentrate the solution, followed by lyophilization to give 421 g of the basic protein composition. The content of basic amino acids in this basic protein composition was 10.7%. Further, the molecular weight of this basic protein was 5,000–23,000 dalton, with an isoelectric point distribution of 7.5–10.0. Each liter of the residual solution was treated with sodium chloride for a final sodium chloride concentration of 0.2 M and 2 M respectively, followed by centrifugation, treatment with a reverse osmotic membrane and lyophilization to give 2 g and 23 g of basic protein compositions, respectively. The content of basic amino acids in this basic protein composition was 15.4% and 11.0% respectively.

EXAMPLE 4

A column packed with 3,000 g of cation exchange resin, sulfonated chitopearl (Fuji-bouseki), was washed with deionized water. After loading 300 l of non-sterilized skim milk onto the column at a flow rate of 100 ml/min., the column was washed with deionized water. The basic protein adsorbed onto the resin was eluted with 0.02M carbonate buffer solution containing 0.87M sodium chloride (pH 6.7). A reverse osmotic membrane was used to desalt and concentrate the eluted solution, followed by lyophilization, and a powdery basic protein fraction was obtained. By repeating this operation 8 times, 2.37 kg of basic protein fraction was obtained. The 2.37 kg of the basic protein fraction was dissolved in 50 l of deionized water and 45 l of the solution was filtered using an ultrafiltration membrane with a molecular weight cut off of 500,000(DDS) to give 60 l of permeated solution. The filtrate was then re-filtered with an ultrafiltration membrane with a molecular weight cut off of 30,000, and desalted and concentrated to give 6 l of a concentrated solution. Further, the solution was treated with a reverse osmotic membrane and lyophilized to give 430 g of the basic protein composition. The content of basic amino acids in this basic protein composition was 15.6%. Further, the molecular weight of this basic protein was 2,000–18,000 dalton with an isoelectric point distribution of 8.0–11.0.

EXAMPLE 5

Fifty grams of the basic protein composition heated at 80° C. for 10 min. in Example 1 was dissolved in 10 l of distilled water, to which 1% pancreatin (Sigma) was added, and incubated at 37° C. for 2 hours. After the reaction, the enzyme was inactivated by heating at 80° C. for 10 min. and 48.3 g of the basic peptide composition was obtained. The basic peptide composition had a molecular weight of less than 10,000 dalton and was comprised of 13.5% of basic amino acids.

EXAMPLE 6

Fifty grams of the basic protein composition treated with ethanol (30% final concentration) in Example 2 was dissolved in 10 l of distilled water, to which 1% pancreatin was added, and incubated at 37° C. for 2 hours. After the reaction, the enzyme was inactivated by heating at 80° C. for 10 min. and 49.3 g of the basic peptide composition was obtained. The basic peptide composition had a molecular weight of less than 9,000 dalton and was comprised of 12.9% of basic amino acids.

Test Example 1

The osteoblast proliferation stimulating activity of the following samples A–N was determined:
Sample A: The basic protein fraction of Reference example 1
Sample B: The basic protein composition heated at 75° C. for 10 min. in Example 1
Sample C: The basic protein composition heated at 80° C. for 10 min. in Example 1
Sample D: The basic protein composition heated at 90° C. for 10 min. in Example 1

Sample E: The basic protein composition heated at 95° C. for 10 min. in Example 1

Sample F: The basic protein composition treated with ethanol (final concentration of ethanol 30%) in Example 2

Sample G The basic protein composition treated with ethanol (final ethanol concentration 30%) in Example 2

Sample H: The basic protein composition treated with ethanol (final ethanol concentration 50%) in Example 2

Sample I: The basic protein composition treated with sodium chloride (final sodium chloride concentration 0.2 M) in Example 3

Sample J: The basic protein composition treated with sodium chloride (final sodium chloride concentration 1.0 M) in Example 3

Sample K: The basic protein composition treated with sodium chloride (final sodium chloride concentration 2.0 M) in Example 3

Sample L: The basic protein composition treated with an ultra-filtration membrane in Example 4

Sample M: The basic peptide composition in Example 5

Sample N: The basic peptide composition in Example 6

Figure 1:
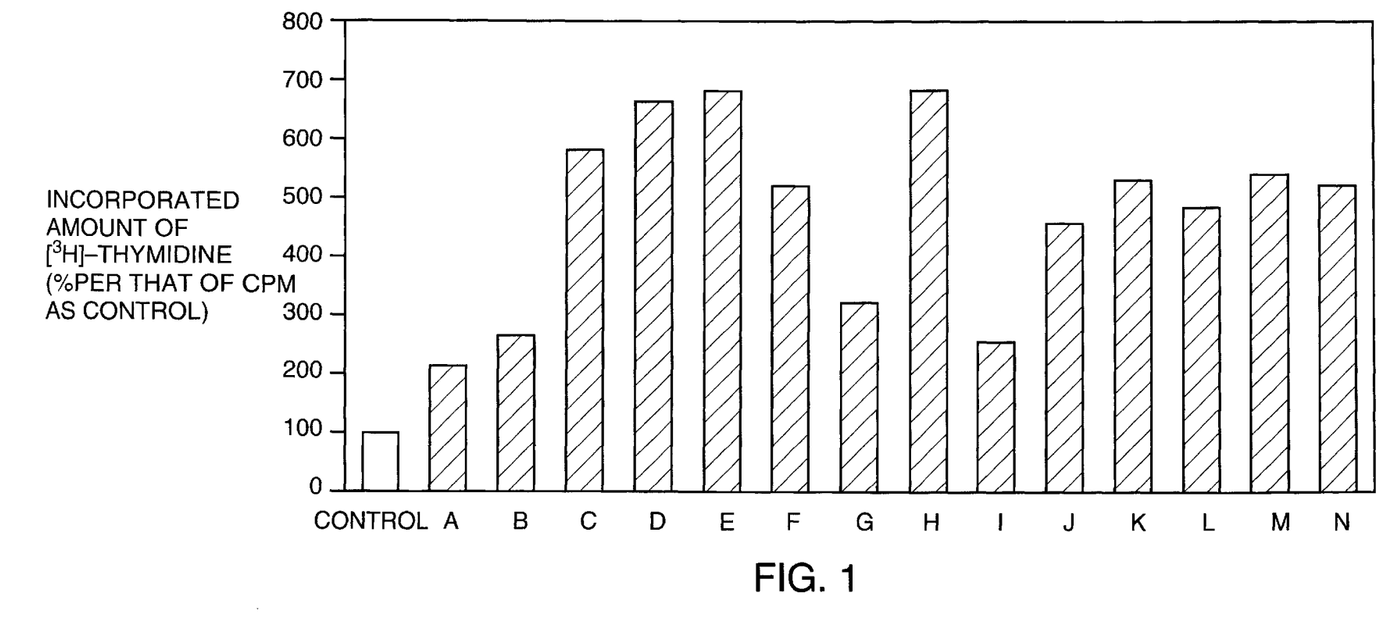
FIG. 1 represents the results of Test example 1 showing the proliferative activity thereof on osteoblasts.

Each well of a 96-well plate was seeded with, $2 \times 10^4$ cells/ml of osteoblast cell line MC3T3-El in a-modified minimum essential medium (a-MEM) containing 10% bovine fetal serum (Flow Laboratories) and cultured in the presence of 5% $CO_2$ at 37° C. for 24 hours. The medium was changed to a-MEM and cultured at 37° C. for 16 hours after adding one of the above samples thereto, so that the final concentration thereof was 10 μg/ml. The cells were labeled with [$^3$H]-thymidine, treated by 0.01% Pronase and collected on a glass filter with a cell harvester, to which liquid scintillation cocktail was added. The amount of [$^3$H]-thymidine incorporated was quantified using a liquid scintillation counter and the results are shown in FIG. 1.

Compared to cultured cells treated with medium only (control), stimulative activity on osteoblast proliferation was enhanced by treatment of cells with any one of the above Samples A–N. In addition, the basic protein composition samples B–N of the present invention had a significantly enhanced osteoblast proliferation stimulating activity compared to that of the basic protein fraction Sample A of Reference example 1.

Similar results to the above were obtained using another osteoblast cell line, UMR.

Test Example 2

The ability of Test Example 1 Samples A–N to stimulate collagen synthesis was examined according to the method of Woessner (Woessner, J. F., Arch. Biochem. Biophys., vol.93, pp440–447, 1961).

Each well of a 96-well plate was seeded with $2 \times 10^4$ cells/ml of osteoblast cell line MC3T3-El in α-MEM containing 10% bovine fetal serum (Flow Laboratories) and cultured in the presence of 5% $CO_2$ at 37° C. for 24 hours. The medium was changed to α-MEM and cultured at 37° C. for 3 days after adding one of the above samples thereto so that the final concentration thereof was 50 μg/ml and the amount of synthesized collagen was determined.

Figure 2:
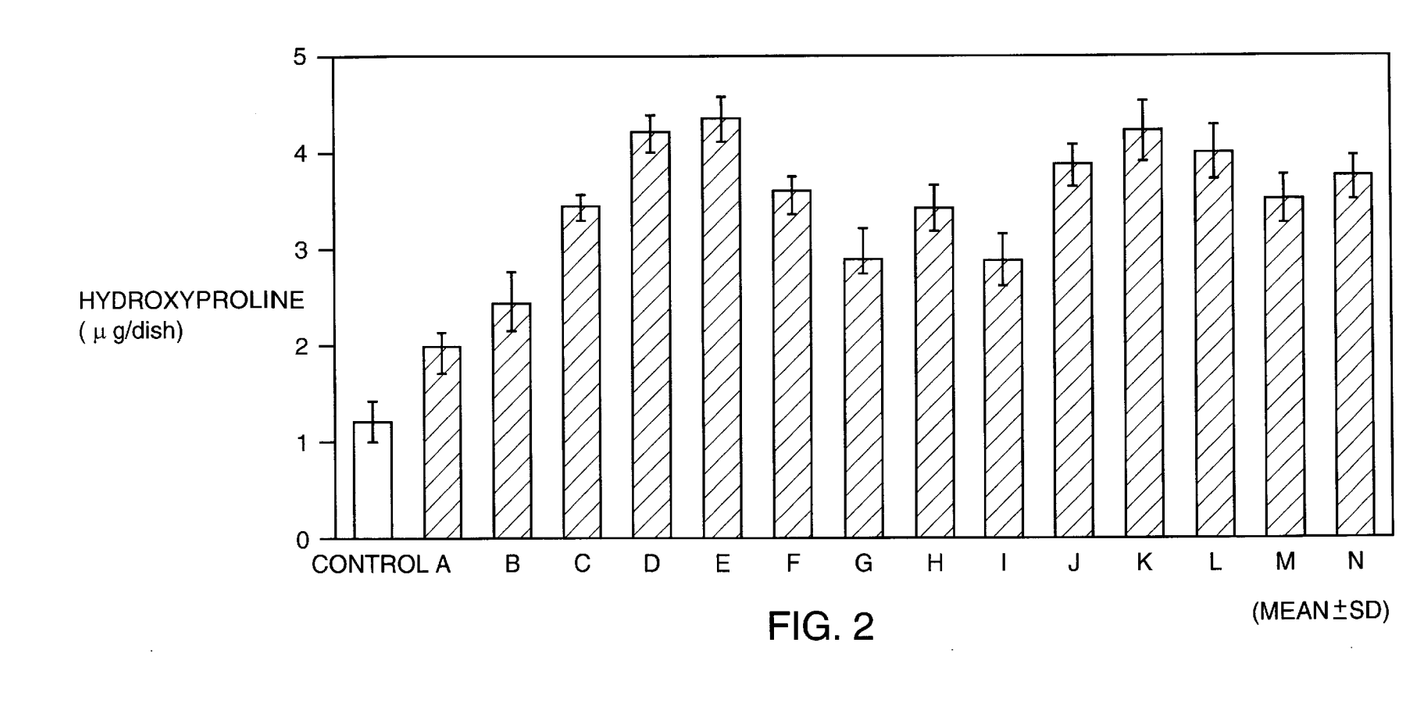
FIG. 2 represents the results of Test example 2 showing the stimulatory activity thereof on collagen synthesis.

The amount of collagen was analyzed by determining the amount of hydroxyproline using p-dimethyl-aminobenzaldehyde after hydrolyzing punctured cells with 6N hydrochloric acid. The results are shown in FIG. 2.

Compared to cultured cells treated with medium only (control), the amount of hydroxyproline increased in response to treatment with any one of the above Samples A–N, suggesting that the basic protein fractions and the basic peptide fractions from A to N stimulate collagen synthesis in osteoblasts. In addition, the basic protein compositions of the present invention (Samples B–N) were found to have a significantly greater collagen synthesis stimulating activity in osteoblasts as compared to that of the basic protein composition (sample A) of Reference example 1.

Test Example 3

Figure 3:
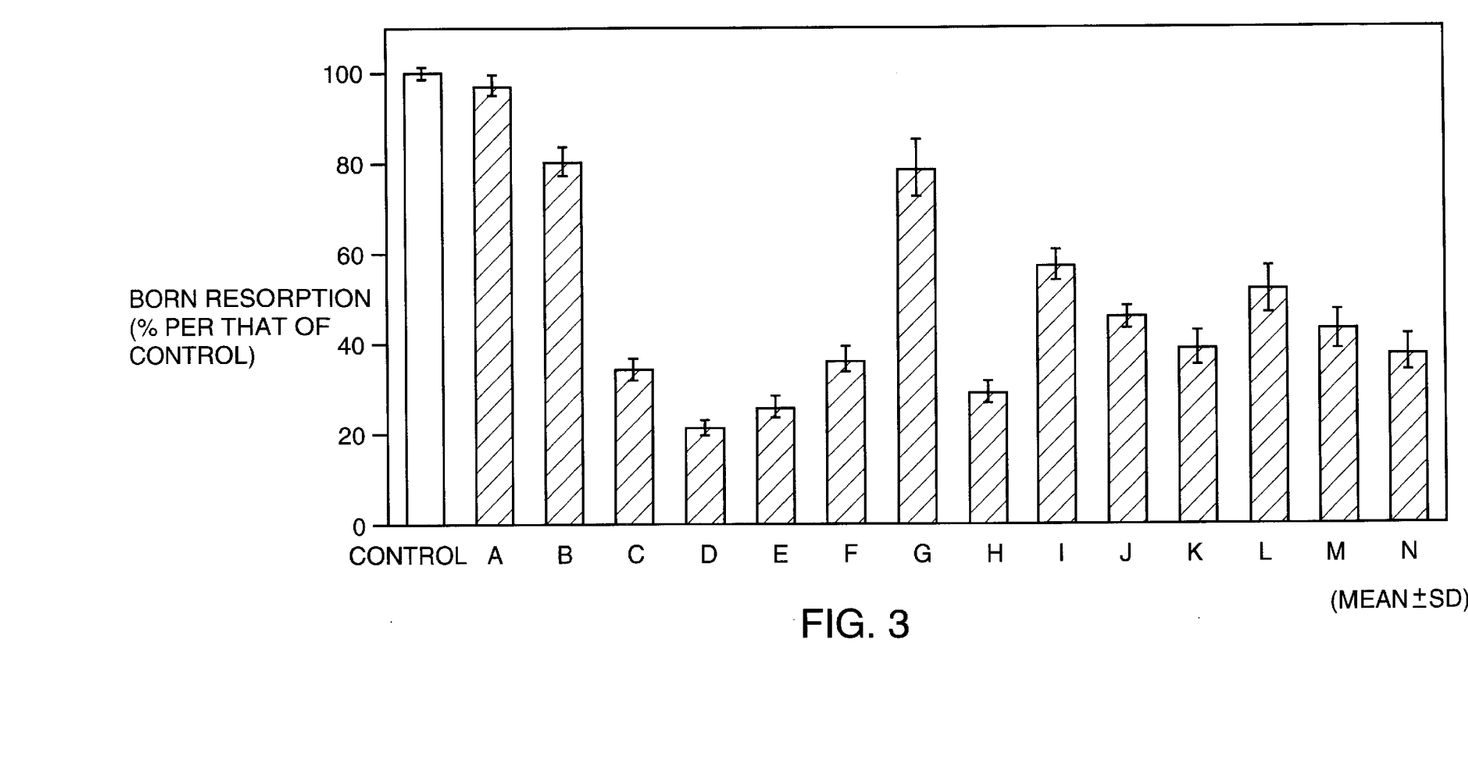
FIG. 3 represents the results of Test example 3 showing the inhibitory activity thereof on bone resorption.

The ability of Test Example 1 Samples A–N to inhibit bone resorption was examined according to the method of Takada (Takada,Y. et al., Bone and Mineral, vol.17, pp. 347–359, 1992). Long bones were obtained from 10–20 day old ICR mice and whole bone marrow cells containing osteoclasts were obtained by removing soft tissue from the bones and mincing the tissue in α-MEM containing 5% bovine fetal serum. About $2 \times 10^6$ of these cells in α-MEM containing 5% bovine fetal serum were placed onto a piece of dentine. Several hours later, α-MEM containing 5% bovine fetal serum containing one of the above test samples was added to the cells, they were cultured for 5 days, and the bone resorptive activity of the osteoclasts were examined. Analysis of bone resorption was carried out by removing cells from a piece of dentine after cultivation thereof, staining them with hematoxylin dye and measuring the area of bone resorptive cavity by morphometrical analysis with PIAS-LA-555. The results are shown in FIG. 3.

Compared to cultured cells treated with medium only (control), a significant bone resorptive activity was observed in the basic protein fractions (samples B–N).

Test Example 4

The bone strengthening activity of the following samples were determined:

Sample C: The basic protein composition heated at 80° for 10 min. in Example 1

Sample F: The basic protein composition treated with ethanol (final ethanol concentration 30%) in Example 2

Sample J: The basic protein composition treated with sodium chloride (final sodium chloride concentration 1.0 M) in Example 3

Sample L: The basic protein composition treated with an ultrafiltration membrane in Example 4

Sample M: The basic peptide composition in Example 5

Sample C+milk calcium

Sample F+milk calcium

Table 1 shows the composition of a basic feed 0.3% of one of the above test Samples A–N was added in place of casein to the composition in Table 1. Milk calcium, described in Japanese published unexamined patent application No. 306622 (1992) was used in place of calcium contained in a mineral mixture.

TABLE 1

| | |
|---|---|
| Sucrose | 49.3 (g/100 g) |
| Casein | 20.0 |
| Corn starch | 15.0 |
| Cellulose | 5.0 |
| Corn | 5.0 |
| Vitamin mixture (including choline) | 1.2 |
| Mineral mixture | 4.5 |

Figure 4:
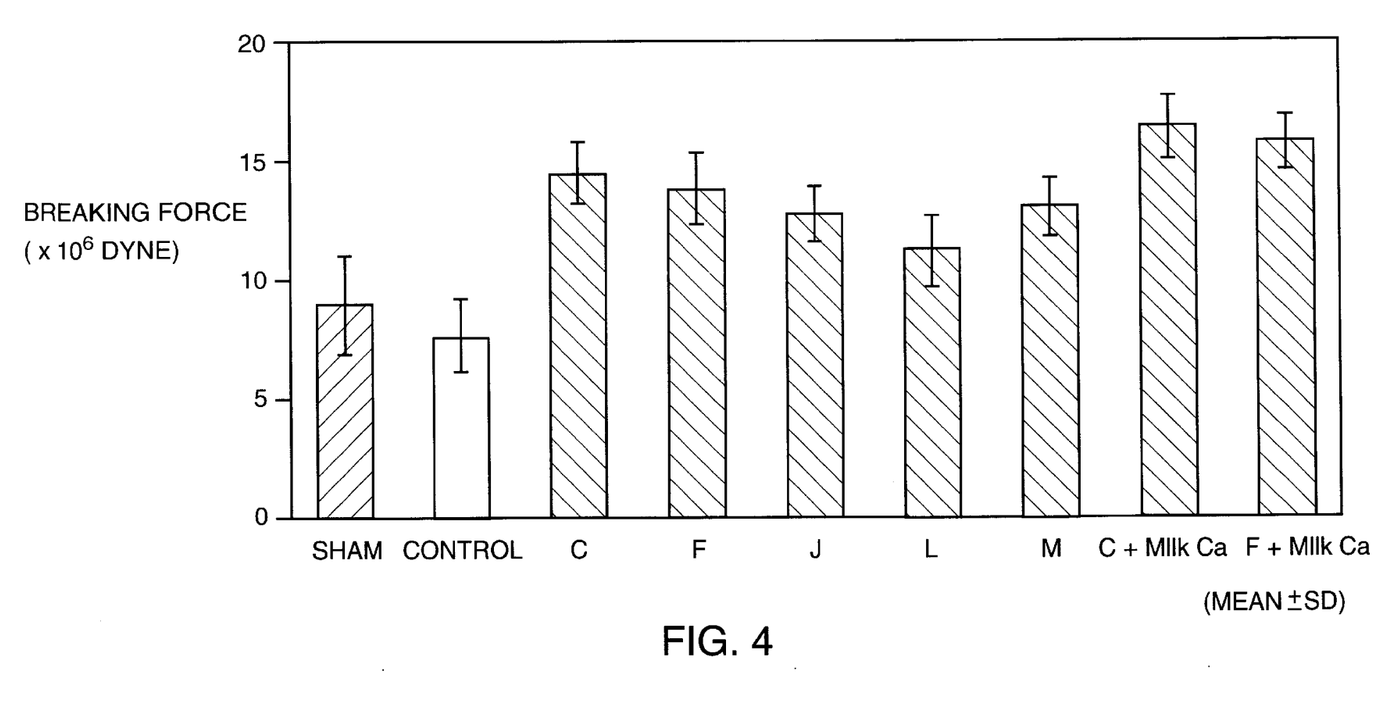
FIG. 4 represents the results of Test example 4 showing the activity thereof on strengthening bone.

Osteoporotic model rats were made by ovarectomy of 6 weeks old female SD rats and feeding with a low calcium diet for two months. Sham rats were also made by sham operation wherein ovaries were not removed. Each sample feed was administered to a group consisting of 7 rats for 1 month. Femurs of rats in each test group were taken after the administration of the test feed and the breaking force of the bones was determined with a threepoint bending rheolometer (RX-1600, A-techno). The results are shown in FIG. 4. The breaking force of the rats' femurs in groups administered with the basic protein composition sample C, F, J, L or M was found to be significantly higher than that for femurs in the control group according to statistical analysis. From these results, Samples C, F, J, L and M of the basic protein composition were found to have an action of strengthening bone activity. In addition, by combining these basic protein compositions with milk calcium, having good absorptivity, their bone strengthening activity was augmented.

EXAMPLE 7

A drink having the ability to stimulate osteoblast proliferation, strengthen bone and inhibiting bone resorption was prepared by mixing the components shown in Table 2 comprising the basic protein composition heated at 80° C. for 10 min in Example 1. (sample C), packing them in a container and sterilizing them by heating.

TABLE 2

| Mixed isomerized saccharide | 15.0 (weight %) |
| --- | --- |
| Fruit juice | 10.0 |
| Citric acid | 0.5 |
| Basic protein composition | 0.5 |
| Flavor | 0.1 |
| Calcium | 0.1 |
| Water | 73.8 |

EXAMPLE 8

A tablet which has the ability to stimulate osteoblast proliferation, strengthen bone and inhibit bone resorption, comprising the ethanol treated basic protein composition (final ethanol concentration 30%) in Example 2 (sample F), prepared by mixing the components shown in Table 3 and formulating it under pressure.

TABLE 3

| Crystalline glucose hydrate | 73.5 (weight %) |
| --- | --- |
| Basic protein composition | 20.0 |
| Calcium | 5.0 |
| Sugar ester | 1.0 |
| Flavor | 0.5 |

EXAMPLE 9

A jelly having the ability to stimulate osteoblast proliferation, strengthen bone and inhibit bone resorption was prepared by mixing the components shown in Table 4 containing ultrafiltrated basic protein composition obtained in Example 4 (sample L), packing it and sterilizing it by heating.

TABLE 4

| Fractose | 20.0 (weight %) |
| --- | --- |
| Granulated sugar | 15.0 |
| Millet jelly | 5.0 |
| Agar | 1.0 |
| Basic protein composition | 0.5 |
| Flavor | 0.1 |

TABLE 4-continued

| Calcium | 0.1 |
| --- | --- |
| Water | 58.3 |

EXAMPLE 10

A processed cheese which has the ability to stimulate osteoblast proliferation, strengthen bone and inhibit bone resorption, comprising the sodium chloride treated basic protein composition (final sodium chloride concentration 1.0 M) in Example 3 (sample J), was prepared by mixing the components shown in Table 5 and sterilizing at 85° C.

TABLE 5

| Gouda cheese | 43.0 (weight %) |
| --- | --- |
| Cheddar cheese | 43.0 |
| Sodium citrate | 2.0 |
| Basic protein composition | 0.5 |
| Milk derived calcium | 1.0 |
| Water | 10.5 |

EXAMPLE 11

A cracker which has the ability to stimulate osteoblast proliferation, strengthen bone and inhibit bone resorption, containing sodium chloride treated basic protein (final sodium chloride concentration 1.0 M) in Example 3 (sample J) was prepared by mixing the components represented in Table 3 with the components shown in Table 6, making dough, and baking it.

TABLE 6

| Wheat powder | 50.0 (weight %) |
| --- | --- |
| Sugar | 20.0 |
| Sodium chloride | 0.5 |
| Margarine | 12.5 |
| Egg | 12.1 |
| Water | 2.5 |
| Sodium bicarbonate | 0.1 |
| Ammonium bicarbonate | 0.2 |
| Calcium carbonate | 0.5 |
| Basic protein composition | 1.2 |

EXAMPLE 12

A dog feed which has the ability to stimulate osteoblast proliferation, strengthen bone and inhibit bone resorption, and comprising the basic protein composition heated at 80° C. for 10 min. in Example 2 (sample C), was prepared by mixing the components shown in Table 7.

TABLE 7

| Soy bean cake | 12.0 (weight %) |
| --- | --- |
| Skim milk powder | 14.0 |
| Soy bean oil | 4.0 |
| Corn oil | 2.0 |
| Palm oil | 28.0 |
| Cornstarch | 15.0 |
| Wheat powder | 8.0 |
| Wheat bran | 2.0 |
| Vitamin mixture | 9.0 |
| Mineral mixture | 2.0 |
| Cellulose | 3.0 |
| Basic protein composition | 1.0 |

We claim:

1. A basic protein composition derived from milk or a milk derived raw material comprising the following properties:
   a) a molecular weight distribution of 2,000–24,000 daltons, as determined by SDS-poylacrylamide gel electrophoresis;
   b) an isoelectric point distribution of 7.5–11;
   c) an amino acid composition comprising at least 10% basic amino acids;
   d) an ability to stimulate osteoblast proliferation; and
   e) an ability to reduce bone resorption activity by at least 20% relative to a protein composition produced by contacting the milk or milk-derived raw material with a cation exchange resin and then eluting the protein composition adsorbed to the resin with an eluate containing 0.1–1.0 M salt.

2. The milk-derived basic protein composition of claim 1, obtained by the following steps:
   a) contacting milk or milk-derived raw material with a cation exchange resin;
   b) eluting from said resin a protein fraction adsorbed thereto with an eluent of 0.1–1.0M salt concentration to produce an eluate;
   c) heating said eluate to at least 75° C. to produce a precipitate; and
   d) separating said precipitate from said eluate to produce a solution containing said basic protein composition.

3. The milk derived basic protein composition of claim 1, obtained by the following steps:
   a) contacting milk or milk-derived raw material with a cation exchange resin;
   b) eluting from said resin a protein fraction adsorbed thereto with an eluent of 0.1–1.0M salt concentration to produce an eluate;
   c) adding ethanol to said eluate to a final ethanol concentration of 10–50% to produce a precipitate; and
   d) separating said precipitate from said eluate to produce a solution containing said basic protein composition.

4. The milk-derived basic protein composition of claim 1, obtained by the following steps:
   a) contacting milk or milk-derived raw material with a cation exchange resin;
   b) eluting from said resin a protein fraction adsorbed thereto with an eluent of 0.1–1.0M salt concentration to produce an eluate;
   c) adding salt to said eluate to a final concentration of 0.2M to produce a precipitate; and
   d) separating said precipitate from said eluate to produce solution containing said basic protein composition.

5. The milk-derived basic protein composition of claim 1, obtained by the following steps:
   a) contacting milk or milk-derived raw material with a cation exchange resin;
   b) eluting from the resin a protein fraction adsorbed thereto with an eluent of 0.1–1.0M salt concentration to produce an eluate;
   c) ultrafiltering said eluate with an ultrafiltration membrane having a molecular weight cut off of more than 30,000 daltons to produce a filtrate; and
   d) recovering said filtrate containing said basic protein composition.

6. A milk-derived basic peptide composition, produced by protease digestion of the milk-derived basic protein composition of any one of claims 1–5.

7. The basic peptide composition of claim 6, comprising basic peptides having a molecular weight of less than 10,000 daltons as determined by SDS-polyacrylamide gel electrophoresis.

8. A drink, food, medicine or feed comprising as an effective component the milk derived basic protein composition of any one of claims 1–5.

9. A drink, food, medicine or feed comprising as an effective component the milk-derived basic peptide composition of claim 6.

* * * * *

UNITED STATES PATENT AND TRADEMARK OFFICE
CERTIFICATE OF CORRECTION

PATENT NO. : 5,976,597
DATED : November 2, 1999
INVENTOR(S) : Takada et al.

It is certified that error appears in the above-identified patent and that said Letters Patent is hereby corrected as shown below:

At box [73], after Assignee,
The text "Fujino Patent Attorney, Tokyo, Japan" should be deleted and replaced with -- Snow Brand Milk Products, Japan--.

Column 12,
Line 40, following claim 9 the text should appear:

--10. A method of reducing bone resorption in a mammal comprising administering to the mammal the composition of any one of claim 1-5 in an amount sufficient to reduce bone resorption in the mammal.--

Signed and Sealed this

Nineteenth Day of June, 2001

*Attest:*

NICHOLAS P. GODICI
*Attesting Officer*  Acting Director of the United States Patent and Trademark Office